United States Patent [19]

Sato et al.

[11] 4,431,853
[45] Feb. 14, 1984

[54] DICYCLOHEXYLETHANE DERIVATIVES

[75] Inventors: Hisato Sato, Tokyo; Haruyoshi Takatsu, Kodaira; Kiyofumi Takeuchi, Urawa; Yutaka Fujita, Yokohama; Masayuki Tazume, Urawa; Hiroyuki Ohnishi, Kanagoe, all of Japan

[73] Assignee: Dainippon Ink and Chemicals, Inc., Tokyo, Japan

[21] Appl. No.: 337,453

[22] Filed: Jan. 6, 1982

[30] Foreign Application Priority Data

Jan. 14, 1981 [JP] Japan ................................. 56-4136

[51] Int. Cl.³ ............................................. C07C 13/00
[52] U.S. Cl. ...................................... 585/20; 585/359; 585/360; 252/299.01
[58] Field of Search ...................... 585/20, 359, 360

[56] References Cited

PUBLICATIONS

Chemical Abstracts, vol. 94:139275C, 1981.

Primary Examiner—Delbert E. Gantz
Assistant Examiner—Cynthia A. Prezlock
Attorney, Agent, or Firm—Sherman & Shalloway

[57] ABSTRACT

A 1,2-di[trans(equatorial-equatorial)cyclohexyl]-ethane derivative of the following general formula

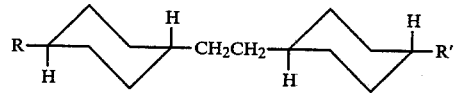

wherein R and R', independently from each other, represent a linear alkyl group having 1 to 10 carbon atoms.

6 Claims, 2 Drawing Figures

DICYCLOHEXYLETHANE DERIVATIVES

This invention relates to novel liquid crystalline compounds useful as electro-optical display materials.

The novel compounds provided by this invention are 1,2-di[trans(equatorial-equatorial)cyclohexyl]ethane derivatives represented by the following general formula

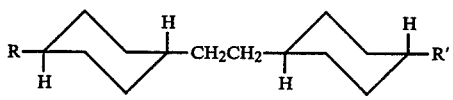
(I)

wherein R and R', independently from each other, represent a linear alkyl group having 1 to 10 carbon atoms.

Typical liquid crystal display cells include field effect mode cells proposed by M. Shadt [Applied Physics Letters, 18, 127–128 (1971)], dynamic scattering mode cells proposed by G. H. Heilmeier et al. [Proceedings of the I.E.E.E., 56, 1162–1171 (1968)] and guest-host mode cells proposed by G. H. Heilmeier et al. [Applied Physics Letters, 13, 91 (1968)] or D. L. White et al. [Journal of Applied Physics, 45, 4718 (1974)]. Liquid crystalline substances used in these liquid crystal display cells are required to have various properties. For example, low viscosities are necessary for increasing response speeds and are the important properties which all these types of cells commonly require. A low anisotropy value ($\Delta n$) of birefringence is the property required for increasing the dichroic ratio of the guest-host mode cells.

The compounds of formula (I) have very low anisotropy ($\Delta n$) of birefringence. Accordingly, by mixing a small amount of the compound of formula (I) with various nematic liquid crystalline materials, the $\Delta n$ of these materials can be effectively reduced. Furthermore, since the compound of formula (I) has a low viscosity, the addition of it in a small amount to various nematic liquid crystalline materials can effectively lead to a decrease in the viscosity of these materials. The compounds of formula (I) can therefore be used as agents for decreasing the viscosities and birefringence anisotropies of various nematic liquid crystalline materials, and are especially useful as liquid crystalline materials for guest-host mode cells.

The compounds of formula (I) in accordance with this invention are produced, for example, by reacting a compound of the formula

(II)

with a trans-4-n-alkylcyclohexyl methyl lithium halide or a trans-4-n-alkylcyclohexyl methyl magnesium halide, preferably a trans-4-n-alkylcyclohexyl methyl magnesium bromide, hydrolyzing the resulting product, distilling the hydrolyzate in vacuum, and recrystallizing the resulting product. This reaction process is schematically shown below (R and R' in the formulae are as defined hereinabove).

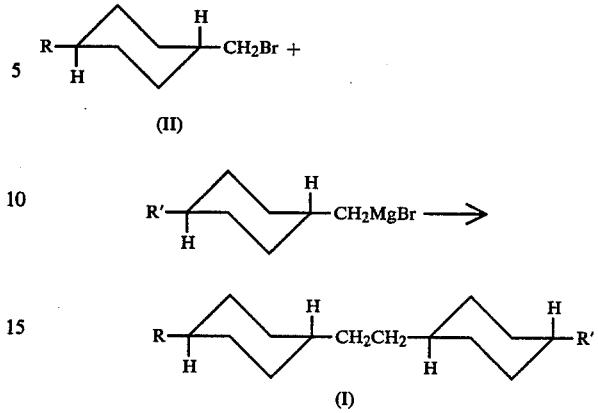

The transition temperatures of typical examples of the compounds of formula (I) produced in this manner are given in Table 1.

TABLE 1

| | | | Transition temperature (°C.) | |
|---|---|---|---|---|
| | Compound | | | |
| No. | R | R' | C → S | S ⇌ I |
| 1 | $C_2H_5$— | $C_2H_5$— | 17 | 29 |
| 2 | n-$C_3H_7$— | n-$C_3H_7$— | 35 | 73 |
| 3 | n-$C_4H_9$— | n-$C_4H_9$— | 20 | 97 |
| 4 | n-$C_5H_{11}$— | n-$C_5H_{11}$— | 49 | 108 |
| 5 | n-$C_7H_{15}$— | n-$C_7H_{15}$— | 53 | 112 |
| 6 | $CH_3$— | n-$C_8H_{17}$— | 15 | 76 |
| 7 | $C_2H_5$— | n-$C_7H_{15}$— | 13 | 73 |

Note
In Table 1, C represents a crystalline phase; S, a smetic phase; I, an isotropic liquid phase; and the arrow, phase transition.

The compounds of formula (I) act effectively as a viscosity reducing agent or birefringence anisotropy reducing agent for all nematic liquid crystals. Hence, the addition of the compounds of formula (I) to nematic liquid crystals can lead to the improvement of the response speeds of various liquid crystalline cells and the display vividness or contrast of guest-host mode liquid crystal cells. Typical examples of such nematic liquid crystals include phenyl 4,4'-disubstituted benzoate, thiophenyl 4,4'-disubstituted benzoate, 4,4'-disubstituted benzylidene aniline, 4,4'-disubstituted azoxybenzene, 4,4'-disubstituted biphenyl, phenyl 4,4'-disubstituted cyclohexanecarboxylate, 4,4'-disubstituted phenylcyclohexane, and 4,4'-biphenyl-cyclohexane.

Table 2 below summarizes the viscosities and birefringence anisotropies of nematic liquid crystal compositions composed of 90% by weight of a mixed nematic liquid crystal (A) having a low viscosity which are now in widespread use and 10% by weight of compounds Nos. 1 to 7 of formula (I) respectively, and of the mixed nematic liquid crystal (A) itself. The mixed nematic liquid crystal (A) consists of

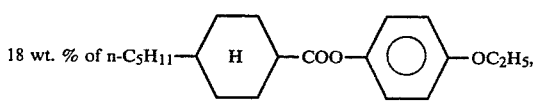

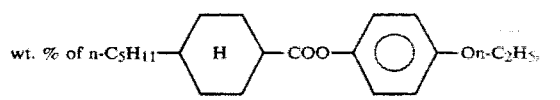 wt. % of n-C₅H₁₁—⟨H⟩—COO—⟨○⟩—On-C₂H₅,

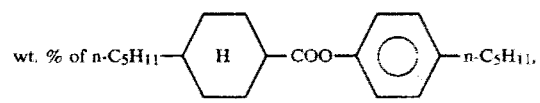 wt. % of n-C₅H₁₁—⟨H⟩—COO—⟨○⟩—n-C₅H₁₁, 18 wt. % of n-C₃H₇—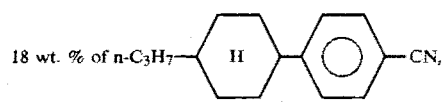—CN, 18 wt. % of n-C₅H₁₁—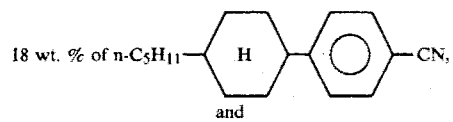—CN, and 18 wt. % of n-C₇H₁₅—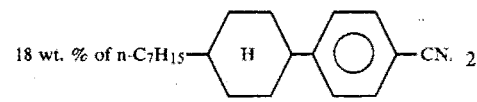—CN.

TABLE 2

| Liquid crystal | Viscosity (centipoises at 25° C.) | Birefringence anisotropy (Δn/25° C.) |
| --- | --- | --- |
| (A) | 20 | 0.0944 |
| (A) + (No. 1) | 15.9 | 0.0871 |
| (A) + (No. 2) | 16.1 | 0.0875 |
| (A) + (No. 3) | 16.4 | 0.0878 |
| (A) + (No. 4) | 16.5 | 0.0879 |
| (A) + (No. 5) | 16.8 | 0.0883 |
| (A) + (No. 6) | 16.3 | 0.0878 |
| (A) + (No. 7) | 16.3 | 0.0877 | t will be understood from the data shown in Table 2 t the addition of a small amount of the compound of mula (I) can greatly reduce the viscosity and birefrigence anisotropy value of the mixed nematic crystal ). The viscosity (20 centipoises/25° C.) and a birefringence anisotropy value (0.0944/25° C.) of the mixed natic liquid crystal (A) are much lower than those of ious average nematic liquid crystal compositions w in commercial use. The compounds of formula (I) /e a high utilitarian value in that they can further atly reduce such low viscosity and birefringence sotropy values of the nematic liquid crystal (A). The effects of this invention are demonstrated by a nparative experiment shown below.

A compound of the following formula (the compound number 8).

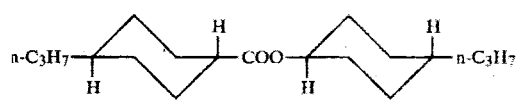

ring a low viscosity and a similar chemical structure he compound of formula (I) [Mol. Cryst. Liq. Cryst. 157 (1980)] was mixed in various proportions with mixed nematic liquid crystal (A). Likewise, the lowing compounds in accordance with this invention e compound number 2)

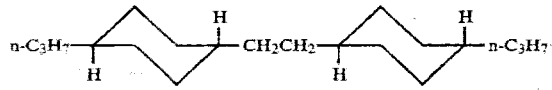

was mixed in various proportions with the mixed nematic liquid crystal (A). The viscosities and birefringence anisotropy values of the resulting two types of nematic liquid crystal compositions were measured.

Figure 1:
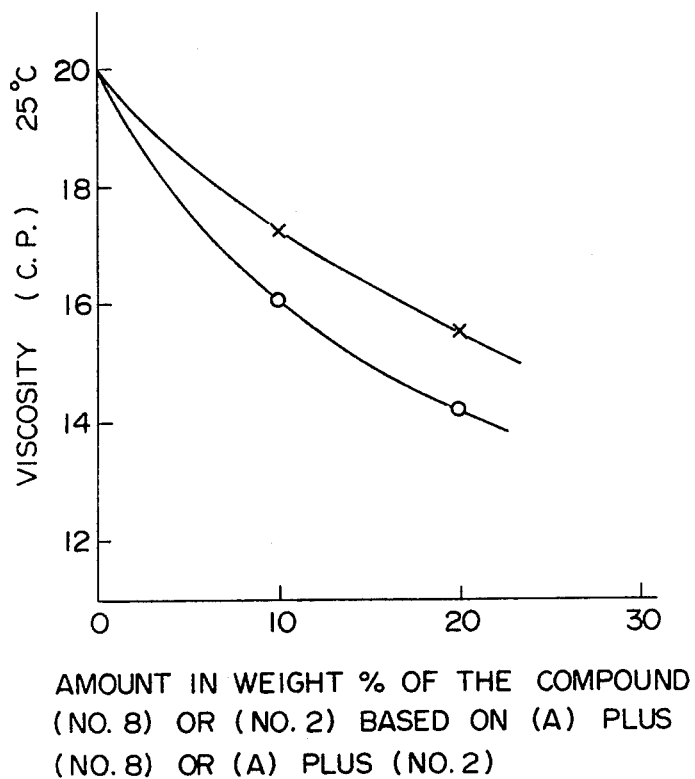
FIG. 1 of the accompanying drawings shows the results of the viscosity measurement and FIG. 2, the results of the birefringence anisotropy measurement.
Figure 2:
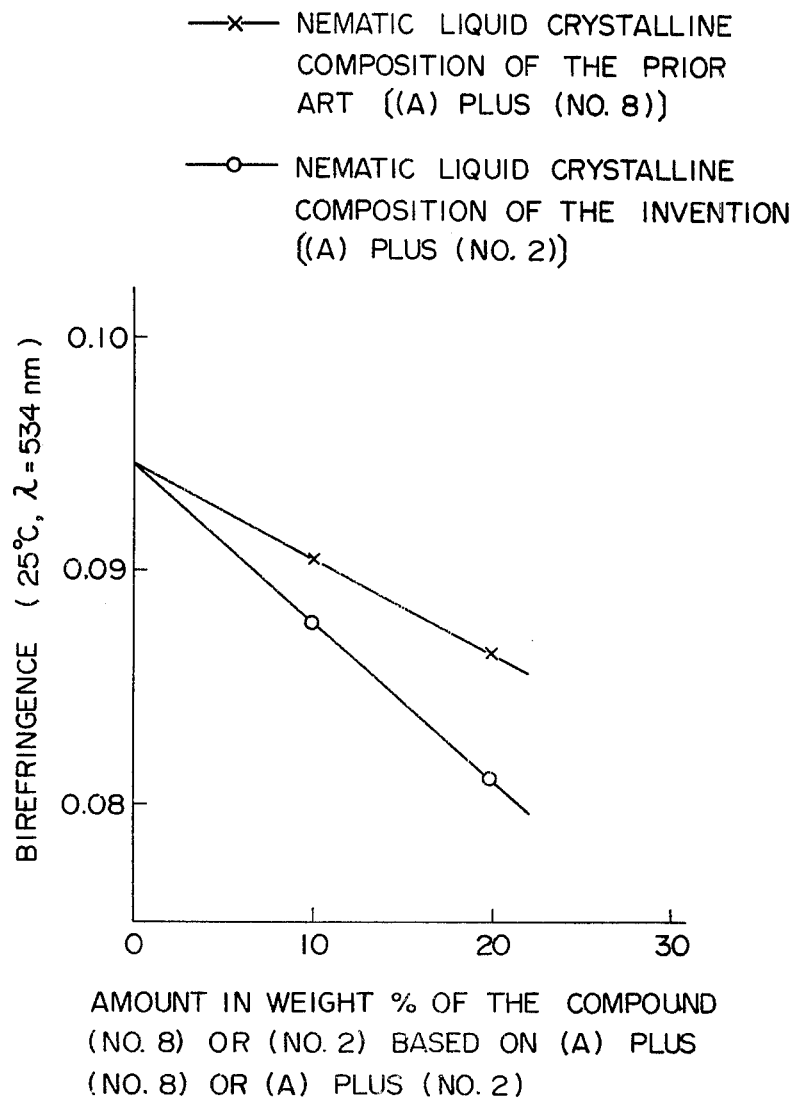

When compounds Nos. 1 and 3 to 7 of the invention were used, similar graphs to that obtained in the case of compound No. 2 were obtained.

The above experimental fact clearly shows that the compounds of formula (I) of the invention can greatly reduce the viscosities and birefringence anisotropy values of nematic liquid crystals as compared with the typical known analogous compound.

There has previously been no compound which can greatly reduce both the viscosity and birefringence anisotropy value of liquid crystals when used in an amount of as small as about 10 to 20%. Accordingly, the compounds of formula (I) in accordance with this invention are very valuable in designing practical liquid crystals by mixing them with known liquid crystals.

The following non-limitative Examples illustrate the present invention specifically.

EXAMPLE 1

Anhydrous ether (80 cc) was added to 2.43 g (0.10 mole) of magnesium, and with stirring, 21.9 g (0.10 mole) of a compound of the following formula

was added. The mixture was refluxed for 1 hour. Then, 21.9 g (0.10 mole) of a compound of the following formula

was added dropwise gradually, and the mixture was refluxed for 5 hours. After the reaction, 200 ml of 0.5 N hydrochloric acid was added dropwise. The reaction mixture was washed with a 5% aqueous solution of sodium bicarbonate and water and then dried over sodium anhydrous sodium sulfate. The ether was then distilled off. The resulting reaction product was distilled and recrystallized from ethanol to give 10.8 g (0.0388 mole) of a compound of the following formula.

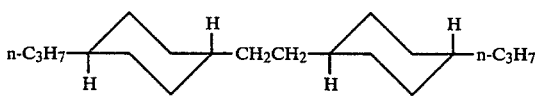

Yield: 38.8%

Transition temperature: 35° C. (C→S), 73° C. (S⇌I)

EXAMPLE 2

In a similar manner to Example 1, the following compounds were prepared.

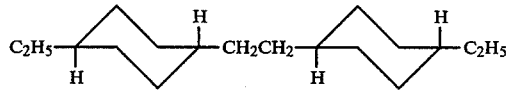

Transition temperature: 17° C. (C→S), 29° C. (S⇌I)

Yield: 32.0%

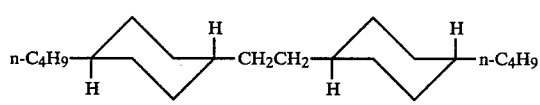

Transition temperature: 20° C. (C→S), 97° C. (S⇌I)

Yield: 35.9%

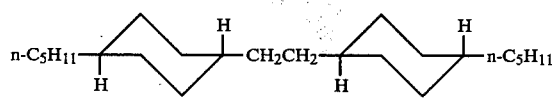

Transition temperature: 49° C. (C→S), 108° C. (S⇌I)

Yield: 37.4%

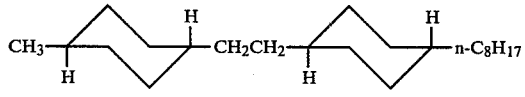

Transition temperature: 53° C. (C→S), 112° C. (S⇌I)
Yield: 32.1%

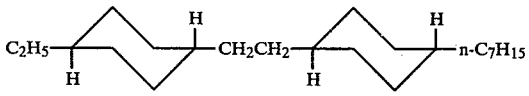

Transition temperature: 15° C. (C→S), 76° C. (S⇌I)
Yield: 31.1%

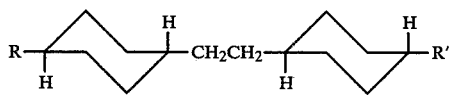

Transition temperature: 13° C. (C→S), 73° C. (S⇌I)
Yield: 30.4%

What we claim is:

1. A 1,2-di(trans(equatorial-equatorial)cyclohexyl)-ethane derivative of the following general formula

wherein R and R', independently from each other, represent a linear alkyl group having 1 to 8 carbon atoms with the proviso that the total number of carbon atoms in R and R' is from 4 to 9 inclusive.

2. The derivative according to claim 1 wherein R and R' are both ethyl groups.

3. The derivative according to claim 1 wherein both R and R' are n-propyl groups.

4. The derivative according to claim 1 wherein both R and R' are n-butyl groups.

5. The derivative according to claim 1 wherein R is a methyl group and R' is an n-octyl group.

6. The derivative according to claim 1 wherein R is an ethyl group, and R' is an n-heptyl group.

* * * * *